US00PP08170P

United States Patent [19]

Perrine

[11] Patent Number: Plant 8,170

[45] Date of Patent: Mar. 9, 1993

[54] *VINCA MINOR* NAMED SUMMERSNOW

[76] Inventor: Carl R. Perrine, 6205 Lansing Ave., Jackson, Mich. 49201

[21] Appl. No.: 609,174

[22] Filed: Nov. 5, 1990

[51] Int. Cl.[5] ..... A01H 5/00

[52] U.S. Cl. ..... Plt./54.1

[58] Field of Search ..... Plt./54.1

[56] References Cited

U.S. PATENT DOCUMENTS

P.P. 6,960 8/1989 MacKenzie ..... Plt. 54

OTHER PUBLICATIONS

Bailey, L. H. "Vinca" *The Standard Cyclopedia of Horticulture* (1935) The MacMillan Co., N.Y. pp. 3470, 3471 (vol. 3).

*Primary Examiner*—James R. Feyrer

*Attorney, Agent, or Firm*—Beaman & Beaman

[57] ABSTRACT

A new *Vinca minor* variety named 'Summersnow' propagated for its contrasting foliage and compact mounding growth habit that is best displayed when grown in full sunlight. The plant is winter hardy requiring no extra care or protection during winter. The foliage is variegated with medium green, light green, white and occasionally yellow blotches randomly occurring on each leaf.

1 Drawing Sheet

BACKGROUND OF THE INVENTION

This new variety of *Vinca minor* hereinafter known as 'Summersnow' originated as a branch sport of 'Bowlesii', a cultivar with dark green leaves and large purple flowers, that occurred as a spontaneous mutant on a container grown plant in a nursery. Subsequent propagations by cuttings have demonstrated that its novel characteristics are retained from generation to generation. Propagation continues at Jackson, Mich., and Perry, Ohio.

The first successful asexual reproduction of 'Summersnow' was carried out by its discoverer, Carl R. Perrine. This was accomplished under controlled conditions at Riverland Nursery, in Jackson, Mich., on Jul. 20, 1987.

The branch sport was cut and dipped in a quick dip solution of 3000 ppm IBA and placed in rooting media and then positioned in a greenhouse under intermittent mist for four weeks. After successful rooting, the plant was held in a cold greenhouse over winter and planted outside in light shade to full sun for further evaluation. Subsequent propagations having been made the following year, allowed the plant to be evaluated under more diverse conditions. Though not all possible conditions have been used, the plant varies only slightly in growth habit with color variations and lack of flower production remaining constant.

The parent 'Bowlesii' plant, which was originally propagated by cutting, has also subsequently been propagated from and it continues to flower and grow in a manner characteristic of the cultivar 'Bowlesii'. It has not shown any propensity to further produce any other mutations while being grown under stock block conditions.

DESCRIPTION OF THE PHOTOGRAPH

The accompanying photograph illustrates this new variety when grown in full sunlight. The brilliant color contrast, compact form, and mounding growth habit are appreciated from the photograph. The photograph was taken with Kodak 200 color film at 11:00 a.m. on a sunny day.

DESCRIPTION OF THE INVENTION

The following traits and characteristics have been repeatedly observed and are determined to be the basic characteristics of 'Summersnow', showing 'Summersnow' to be a new and distinct cultivar. The color codes set forth below correspond with Munsell Book of Color by A. H. Munsell, Macbeth Division of Kollmorgen Corporation, Baltimore, Md. 21218.

1. The stems arise vertically from the crown 3–6 inches, are stiff and will have two to three pairs of opposite nodes. The stem apex will hold four opposite leaves which combine with other stems coming from the crown to form a dense canopy, while the typical trailing vine stems which also come from the central crown next to growing media, extend out along the surface. As these stems come in contact with moist growing media, rooting occurs and new crown centers emerge.
2. Typical stems are herbaceous and uniformly colored 5 GY 6/8. They are rounded, striate and approximately 1/32 to 1/16 of an inch in diameter.
3. Internodes range from ¾ to 1 inch in length.
4. The variegation in leaf coloration is continuous, and characteristically of unpredictable pattern, but always marginal in character and location. The central portions of leaves are of a deep green color and of unpredictable patterns which occupy normally about 80 to 85% of the surface area of mature leaves; with leaf margins being of a contrasting near-white coloration. Minor expanses between these sharply contrasting color zones may contain smaller, irregular blotches or blocky patterns of an intermediate yellow-green color, giving individual leaves a laminated appearance when closely viewed. This development and effect may be due to overlying mesophyll cell layers which differ greatly in chlorophyll content, a condition usual in stable chimerias of this type. Evergreen foliage is simple, arranged in opposite pairs. As bud shoots elongate, early leaves have medium green 10 GY 8/4 centers with white 5Y 9/2 to yellow 7.5Y 9/4 margins. As growth continues and leaves mature, the centers darken to a green 10 GY 5/6 which occupies approximately 35–45% of the total leaf surface. The color gradually lightens to a green 10 GY 8/4 and 5Y 6/8 which usually occupies 15–20% in equal proportions, and then finishes out to white 5Y 9/2 margins. This occurs when grown in full to half shade. When grown in full sun, the margins will have a slight shade of yellow 7.5Y 9/4. The margins range in size from 1/16 to 3/16 of an inch. Though each leaf is unpredictable in the amount and shape of coloration, each leaf is predictable in that each color is present in all leaves. An all white stem occasionally occurs, but does not persist.

5. Leaf blades are ovate to elliptical, apex obtuse in young leaves to acute in maturation. Leaf bases are acute. Leaves are cupped, occasionally wavy with margins held slightly higher than midrib. Mature foliage is typically 1¼ inch long by ⅝ to ¾ inch wide. Leaf margins are entire. The mature foliage is held closely by short petioles measuring approximately ⅛ of an inch and are 5 GY 6/8 in color.
6. Midrib are prominent, white 5Y 9/2. Primary branches are held at acute angles to the midrib and are 10 GY 5/6 in color, disappearing as they reach into variegated areas.
7. Leaf underside are green 10 GY 8/4 consistent to white 5Y 9/2 margins.
8. 'Summersnow' annual growth, when planted in light shade to full sun, with adequate moisture, can be expected to reach 6–8 inches horizontally and 3–6 inches of dense vertical growth from central crowns, forming a mounding mat.
9. The plant is unlike typically known varieties in that after four years of observation, plants grown in full sun to full shade, have no flower, no flower bud, and consequently, no seed has been seen.

The most closely related cultivars which exist known to the discoverer are *Vinca minor* Argenteo-variegata and 'Ralph Shugert' as disclosed in U.S. Plant Pat. No. 6,960. Both of these cultivars are variegated as is 'Summersnow', however, 'Ralph Shugert' has wide deep green leaf centers to thin white margins, reflexed leaves and deep purple flowers. The Argenteo-variegata cultivar is green with creamy white variegations occurring throughout the flat leaf; however, 'Summersnow' has a cupped shaped leaf with four colorations moving from the center to the margins. The two previous cultivars produce flowers, and 'Summersnow' does not.

Further distinctions of 'Summersnow' over 'Ralph Shugert' are that 'Ralph Shugert' has only two colors, dark green and white, while 'Summersnow' has four colors. 'Summersnow's' petiole is approximately one inch in length, while 'Ralph Shugert's' petiole is ½ inch. The 'Ralph Shugert' stem is 3/32 of an inch thick, while 'Summersnow' is about 1/16 of an inch. 'Ralph Shugert' grows in a spread out pattern, while 'Summersnow' grows in vertical mounding patterns.

Propagation of 'Summersnow' is easily achieved by division, layering and by cutting (using stem with basal node preferred). However, all white stems should not be used in that they do not root.

I claim:

1. A new and distinct form of *Vinca minor* substantially as herein shown and described named 'Summersnow', characterized in particular by its variegated foliage with variations of green and white having profuse compact growth in full sunlight.

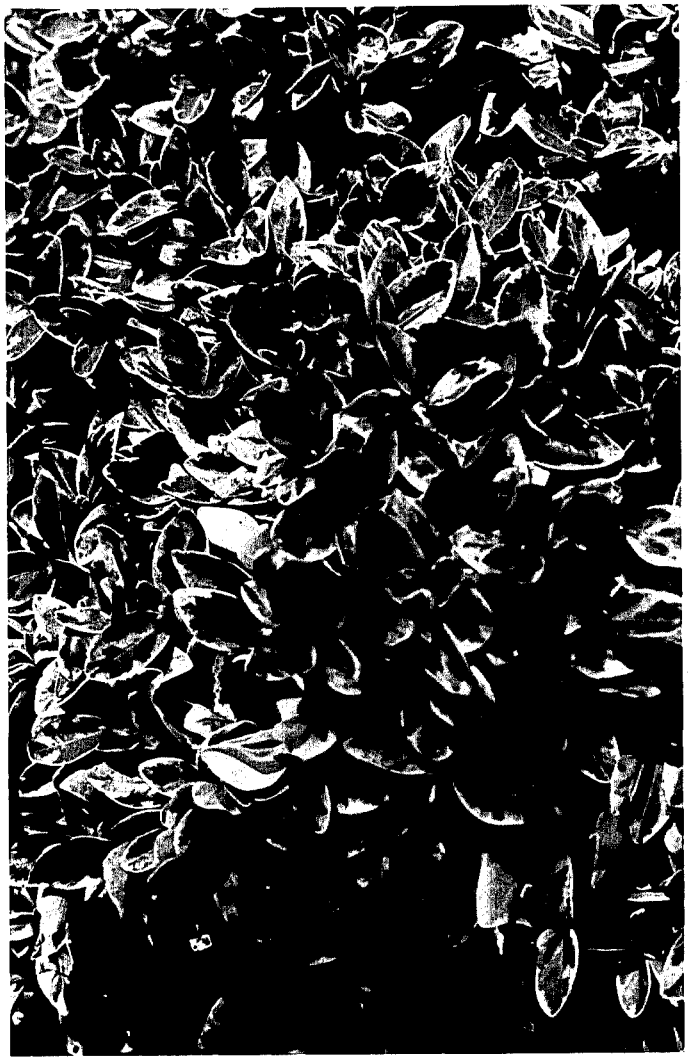

* * * * *